(12) United States Patent
Mühlbauer et al.

(10) Patent No.: US 6,315,164 B1
(45) Date of Patent: Nov. 13, 2001

(54) METHOD AND DEVICE FOR GENERATING A MULTI-COMPONENT COMPOUND, IN PARTICULAR FOR DENTAL PURPOSES

(75) Inventors: Wolfgang Mühlbauer; Hans Hörth, both of Hamburg (DE)

(73) Assignee: Ernst Muhlbauer KG, Hamburg (DE)

( * ) Notice: Subject to any disclaimer, the term of this patent is extended or adjusted under 35 U.S.C. 154(b) by 0 days.

(21) Appl. No.: 09/437,353

(22) Filed: Nov. 9, 1999

(30) Foreign Application Priority Data

Nov. 11, 1998 (EP) .................................................. 98121416

(51) Int. Cl.⁷ .............................. B67D 5/08; B67D 5/52
(52) U.S. Cl. ........................... 222/63; 222/325; 366/189; 366/177.1
(58) Field of Search .................................. 222/1, 63, 333, 222/325, 326, 327, 390; 366/189, 190, 177.1, 181.4, 181.5, 181.8

(56) References Cited

U.S. PATENT DOCUMENTS

| | | | |
|---|---|---|---|
| Re. 26,180 | * 4/1967 | Frenzel et al. | 222/327 |
| 4,171,072 | * 10/1979 | Davis, Jr. | 222/326 |
| 4,335,834 | * 6/1982 | Zepkin | 222/63 |
| 4,341,327 | * 7/1982 | Zeitz | 222/63 |
| 4,731,058 | * 3/1988 | Doan | 222/63 |
| 5,775,539 | * 7/1998 | Bates et al. | 222/327 |
| 5,806,739 | * 1/1999 | Cannon | 366/189 |
| 5,909,830 | * 6/1999 | Bates et al. | 222/327 |
| 5,921,437 | * 7/1999 | Takachi | 222/63 |
| 6,047,861 | * 4/2000 | Vidal et al. | 222/327 |
| 6,135,327 | * 10/2000 | Post et al. | 222/333 |

* cited by examiner

*Primary Examiner*—Tony G. Soohoo
(74) *Attorney, Agent, or Firm*—Alix, Yale & Ristas, LLP

(57) ABSTRACT

Method and device for generating a multi-component compound, in particular for dental purposes, by pressing its components out from exchangeable cartridges (5) which are arranged alongside one another and open into a mixer (10). To ensure that the mixing quality is not adversely affected by the advance speed differing depending on viscosity and friction ratios, the advance speed is constantly kept at a predetermined value according to the invention. This is preferably achieved by means of a unit (30) which is assigned to the drive motor (15). This unit (30) can also be used for driving the motor, depending on the load, either at a low speed assigned to the normal advance or at a higher speed assigned to the return movement.

9 Claims, 1 Drawing Sheet

METHOD AND DEVICE FOR GENERATING A MULTI-COMPONENT COMPOUND, IN PARTICULAR FOR DENTAL PURPOSES

FIELD OF THE INVENTION

The present invention relates to multi-component dental compounds and is more particularly concerned with a device and method of forming such a material.

BACKGROUND OF THE INVENTION

To produce hardening multi-component impression compounds for use in dentistry, components are employed which are contained in cylindrical cartridges and which are pressed out synchronously and mixed together (EP 87 029 A1, EP-A-492 413, WO98/44860). The cartridges are designed as storage cylinders whose front ends form nozzle openings, which are each connected to an inlet opening of a mixing nozzle, and whose rear ends are open for receiving a plunger which is advanced inside the cylinder in order to press out the compound. To do this, equipment is used into which the cartridges connected to or to be connected to the mixing nozzle are introduced, and which has, for each cartridge, a stamp which acts on its plunger by way of the rear open end of the cartridge. To achieve a constant mixing ratio, the stamps are mechanically connected to one another for synchronous movement and are provided with a common electric drive mechanism. The latter comprises a coupling which can be released so that the stamps can be withdrawn from the cartridges by hand if they are to be changed. This change takes place if the cartridges are empty or if the type of impression compound is to be changed.

The mixers used are usually dynamic mixers. These are oblong, cylindrical or conical containers in which mixer vanes revolve and to whose one end the components to be mixed are delivered, and from whose other end the mixed compound emerges through a nozzle opening. At the delivery end of the container, the mixer shaft is equipped with a coupling part which, with the complementary coupling part of a drive shaft provided in the equipment, forms a coupling which is closed by attachment of the mixer to the equipment. Instead of a dynamic mixer with revolving mixer vanes, it is also possible to use a static mixer which is connected in the same way to the equipment and in which baffle plates are arranged which effect the mixing of the components as they flow through.

Until recently, the production of impression compounds almost exclusively used components of like viscosity. When changing over to compounds whose components have a different viscosity than the conventional components, or in which the viscosities of the components to be mixed differ greatly from one another, a deterioration in mixing quality is observed, and the reaction to this is to use different mixers. The disadvantage of this is that different mixer nozzles have to be kept in stock for different multi-component compounds, and replacement of the mixer nozzles can lead to errors being made. This is not only inconvenient, but also entails the risk that poor mixing will cause uncured material to drip into the patient's pharynx or, as a result of punctiform overheating of the material, the patient may suffer burns.

SUMMARY OF THE INVENTION

The invention is therefore based on the object of ensuring a satisfactory mixing result and of simplifying the overall handling, independently of the type of components to be mixed.

Accordingly, a method for generating a multi-component compound, in particular for dental purposes, is characterized by the fact that the advance speed of the plungers in the storage cylinders containing the components in pressing-out mode is regulated constantly at a predetermined value. The load state of the drive mechanism is ascertained. The drive mechanism is driven at a higher return speed or feed speed in the absence of a load. Thus, on the one hand, there is no need for manual return of the plungers when changing the cartridges, and, on the other hand, the change of cartridges is made considerably quicker and thus handling as a whole is improved This is particularly important when the dental surgeon finds, when mixing impression compound, that the cartridges are empty, before the necessary position is reached. The change of cartridges then has to be done very quickly so that the position can be obtained from the new cartridges within the drip time of the mixture.

The part of the invention concerning the pressing-out mode is based on the recognition that a different viscosity of the components not only has an effect on the rheology conditions in the mixer, but also on the dwell time therein. By constantly regulating the advance speed, a constant mixing time is obtained. In this way, the differences in the mixing result can be largely reduced, and to an extent sufficient for practical purposes. This also compensates for differences which (although the reason for them was not known) were hitherto attributed to randomly different friction ratios of the plungers in the cartridges and to the resultant different advance speeds. In a two-component mixer of similar construction (EP 87029 A1), although the absolute advance speed can admittedly be varied, regulation for maintaining the displacement speed is not provided for. The described effect achieved by the invention is particularly marked when using dynamic mixers; but the constancy of the mixing result is also improved when using static mixers.

For regulating the advance speed, electronic units are available which, used on electric motors, make it possible to measure and maintain the speed of rotation in the pressing-out mode at little cost, for example by regulating the voltage of direct-current motors or modifying the frequency in the case of alternating-current motors. Without any great additional expenditure, this regulating unit can also be designed, in addition to other tasks, for ascertaining, according to the invention, the load state of the electric motor, in which case the latter is run at a higher speed if it is not loaded. This detection of the load state can be done in a simple way by measuring the current consumption. If, in order to return the stamps, the drive mechanism is reversed, the electronic regulating unit ascertains that the drive mechanism is not loaded and ensures that the return movement can take place at high speed. If, conversely, after the cartridges have been changed, the device is switched on again and the stamps advanced, freedom from load is again ascertained as long as the stamps have not yet reached the plungers, and the rapid drive speed is adopted. The result of this is that the withdrawal of the stamps from the plunger before cartridge exchange and their advance movement to the plunger after cartridge exchange each take place in a rapid movement The return movement of the stamps upon complete emptying of the cartridges can be automatically initiated by the equipment being provided with a sensor which detects the position which the stamps take up when the cartridges are completely empty. This sensor acts on an electronic unit, for example the regulating unit according to the invention, which then reverses the drive mechanism into the return direction.

In known equipment, the coupling mechanism between the mixer shaft and the mixer drive mechanism, provided for the latter in the equipment, is designed such that the mixer shaft has, on the drive side, a polygonal bore into which there engages a corresponding polygonal attachment arranged at the end of the drive shaft on the equipment side. When attaching the mixer nozzle, care must be taken to ensure that the polygonal attachment engages correctly in the polygonal bore. It is only when this has been ensured that the mixer nozzle can be securely connected to the equipment. This demands a certain amount of attention which is deemed inconvenient when—as is generally the case in medical practice—there are more important things to be considered. The invention thus also seeks a possible way of simplifying attachment of the mixer nozzle. It achieves this through the combination of two features. First, one of the two coupling parts is able to deviate from the other in the longitudinal direction counter to a spring force and/or the drive-side coupling part is completely withdrawn in the state in which the mixer nozzle is to be changed. Second, when the equipment is switched on, it is ensured that the drive shaft moves very slowly so that, under the spring force or while it is being pushed out, it has sufficient time to find, and to mesh correctly into, the relative position of rotation provided for the coupling setting in relation to the other coupling part. The high speed of rotation of the mixer during the normal pressing-out and mixing mode is not suitable for coupling-in. However, since this high speed of rotation of the mixer is only needed when the advance stamps have reached the cartridge plungers and the advance drive mechanism is loaded, it is possible to make the reversing of the speed of rotation of the mixer drive shaft also dependent on the load state of the advance drive mechanism. It is thereby ensured that the mixer drive mechanism operates at a reduced speed if there is no load. This feature is deserving of protection independently of the preceding features. At the same time, in the case of a rapid reverse movement, the drive mechanism of the mixer shaft can be automatically stopped. stopped.

BRIEF DESCRIPTION OF THE DRAWING

The invention is explained in greater detail below with reference to the drawing which shows an advantageous illustrative embodiment. The single FIGURE of the drawing shows a perspective overall view of the equipment.

DETAILED DESCRIPTION OF THE PREFERRED EMBODIMENT

Figure 1:
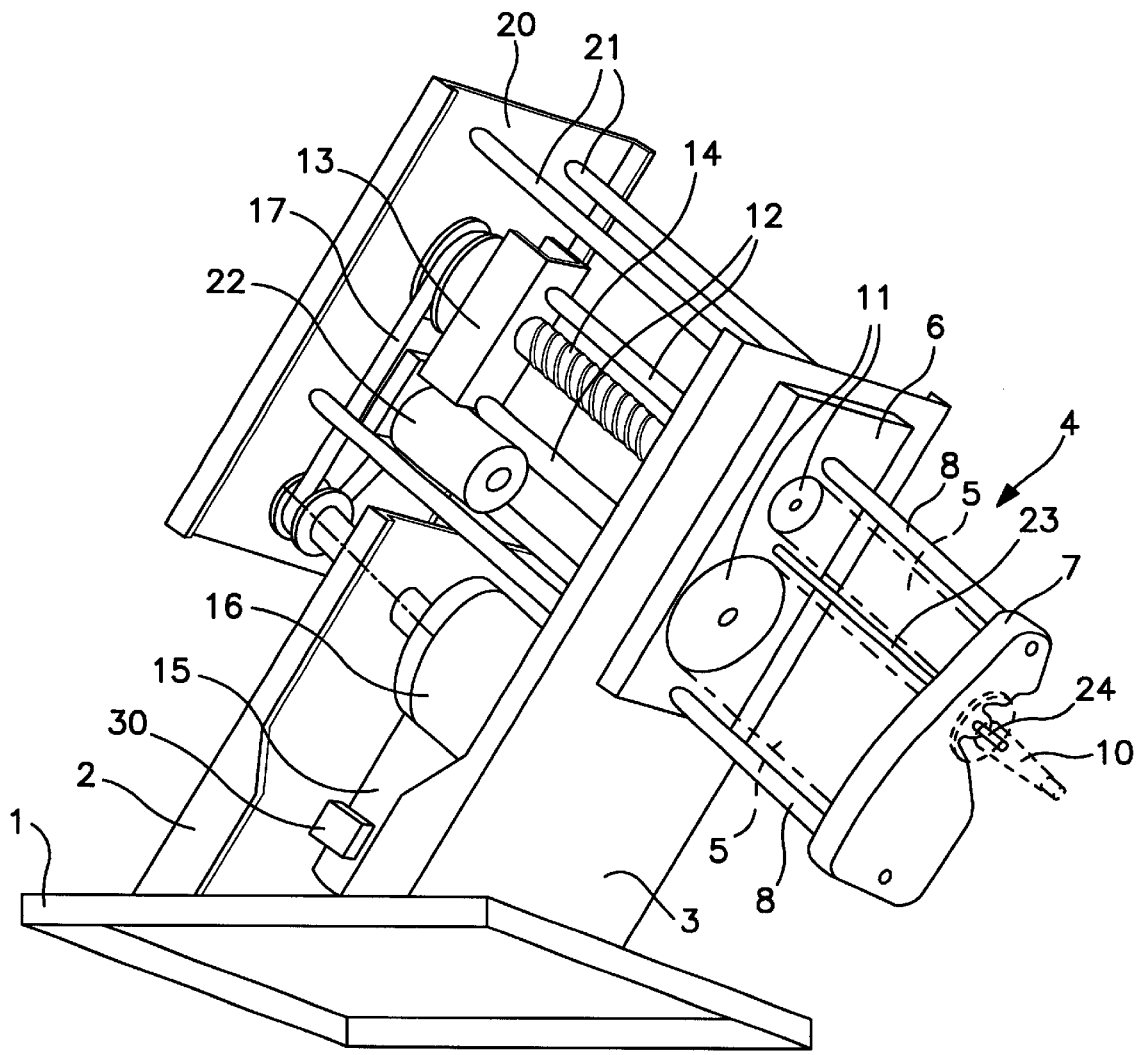

Rising from a base part 1 are the support plates 2, 3. A holder 4 is provided on the latter for cartridges 5, indicated by dot-and-dash lines. In this context it is of no importance whether the cartridges, which are preferably of cylindrical design, are filled directly with the components or receive an optionally exchangeable tubular bag containing the components.

The holder 4 comprises a rear holder plate 6 and a front holder plate 7 which are held together by anchors 8. The cartridges 5 can be fitted between these. Further holding means (not shown) can be provided to act on the lateral positioning of the cartridges 5.

On the front holding plate 7 there is a unit (not shown) for arranging a mixer nozzle 10, indicated by dot-and-dash lines. This has, at its end facing the holding plate 7, two inlet openings which communicate in a known manner directly or indirectly with the outlet openings of the cartridges 5. The claimed feature, namely that the cartridges are arranged alongside one another, is intended only to signify that they are arranged such that they can be operated simultaneously and synchronously. A positional restriction going beyond this, for example restriction to a parallel arrangement, is not thereby intended, although this is obviously advantageous.

The cartridges 5 contain plungers. These can optionally be omitted if the cartridges contain foil bags. The stamps then take the place of the plungers mentioned in the claim. For advancing the plungers or the rear face of the bags, the equipment has stamps 11 which, in the drawing, are shown in the state in which they are retracted into the rear holding plate 6 for the purpose of changing the cartridges. They are arranged at the front end of stamp rods 12, whose rear ends are secured rigidly in a cross bracket 13 which, by means of a threaded spindle 14, can be advanced in the direction of the mixer nozzle or withdrawn in the opposite direction. The stamps 11 can optionally be changed if cartridges of different diameter are to be used. Their distance from one another can also be variable. When the cartridges 5 are fitted in the equipment, the stamps 11 are advanced by advancing the cross bracket 13 until they reach the plungers in the cartridges 5. This advance movement can be triggered automatically by the insertion of the cartridges or can be triggered manually by switching on the equipment.

For the advance and return of the threaded spindle 14, a motor 15 with gear 16 is provided, the drive movement of which is transmitted to the threaded spindle 14 via a belt transmission 17. For mounting the threaded spindle 14 and the annular discs belonging to the belt transmission 17, arrangements (not shown) are provided which are disposed on the plate 3 and on a further frame plate 20 which is connected rigidly to the plate 3 via columns 21.

A further motor 22 is arranged on the plate 20 and is connected (in a manner not shown) on the drive side to a mixer drive shaft 23 which lies between the plates 3 and 20 coaxially within the threaded spindle 14, is guided between the cartridges 5 from the rear holding plate 6 to the front holding plate 7, and is mounted in the latter It protrudes from the front holding plate 7 in the form of a projection 24 which, for the purpose of rotational connection to the mixer shaft (not shown), is of polygonal design (not shown), for example. The shaft projection 24 can be pushed back counter to a spring force until it no longer protrudes from the front holding plate 7. It can also be designed in such a way that when the stamps 11 are completely retracted for the purpose of cartridge exchange, it is likewise retracted into the front holding plate 7 in order to make it easier to attach a new mixer nozzle 10.

An electronic unit 30 is provided and is indicated diagrammatically by 30. The first function of this electronic unit is to constantly regulate the speed of rotation of the motor at a predetermined value when the motor is in pressing-out mode and loaded. This is the function which guarantees the constant mixing result.

A second function of the electronic unit 30 is to measure the current consumption of the motor 15 in order to ascertain whether the latter is loaded or unloaded. In the former case, it is to be assumed that the stamps 11 are bearing on the cylinders of the cartridges 5 and the pressing-out resistance of the cartridges is causing the high current consumption measured by the unit 30. In this case, the electronic unit 30 ensures that the motor 15 is driven at the predetermined advance speed.

If, by contrast, the electronic unit ascertains that the current consumption lies below a value which is normally achieved only when the drive is loaded, it ensures that the motor 15 is driven at a higher speed (for example ten times faster) This applies independently of the direction of rotation of the motor 15.

In the third place, the electronic unit 30 ensures that the motor 22 is driven at a high mixing speed if the drive 15 is loaded. Conversely, it ensures that the motor 22 is driven at a substantially lower speed (for example at a tenth or a twentieth of the mixing speed) if the motor 15 is not loaded in the advance mode. In reverse mode, the drive of the mixer is automatically stopped.

A sensor (not shown) is arranged in such a way that it responds when the advance stamps 11 reach their furthest advanced position, which corresponds to complete emptying of the cartridges 5. If the sensor responds in this position, it causes the electronic unit 30 to reverse the direction of rotation of the motor 15 so that the stamps 11 are drawn back from the cartridges, and in a rapid movement, because they are not loaded at that time. A second sensor (not shown) ascertains when the stamps 11 have reached their completely retracted position shown in the FIGURE. It then causes the motor 15 to stop. The withdrawal of the stamps 11 can also be triggered manually with the aid of a switch (not shown) if cartridges are to be changed before they are empty.

When the stamps 11 are retracted, the cartridges 5 can be changed. The motor 15 is started up again automatically after the insertion of the new cartridges or by manual means. Since the stamps 11 are at first not loaded, they advance in a rapid movement until they reach the plungers of the cartridges 5. The current consumption then increases and the electronic unit 30 switches the motor 15 to its low rotational speed, which is to be kept constant.

When the stamps 11 are retracted, the projection 24 of the mixer drive shaft 23 is also preferably retracted so that the mixer nozzle 10 can be easily changed. When the advance movement of the stamps 11 commences after the cartridges have been changed, the motor 22 is also started up, initially at a low speed as long as the electronic unit 30 does not detect any load state. The shaft projection 24 of the mixer drive shaft 23 then has sufficient time to find the appropriate engagement position in relation to the coupling part of the mixer shaft and, as a result of the spring pressure loading it, to mesh into the coupling position. Only when the stamps 11 have reached the plungers of the cartridges 5 and the electronic unit 30 accordingly detects the load state is the motor 22 accelerated to the high speed of rotation which corresponds to the mixer mode. At the end of an application, the advance is stopped by pressing a button, and in this way a slight return movement of the motor 15 is triggered at the same time, which relieves the load on the system.

What is claimed is:

1. A method for operating a dental appliance comprising an electric drive, a mixer and a plurality of exchangeable parallel tubes that open into the mixer, each tube containing a component of a multi-component dental compound and including a plunger, the dental appliance being of the type that generates the multi-component dental compound by means of common advance of the plungers by the electric drive, the electric drive having a load state when advancing the plungers, said method comprising the steps of:

determining the load state of the electric drive;

maintaining the electric drive at a predetermined constant speed if the drive is loaded; and advancing the speed of the electric drive to a no-load speed that is faster than said predetermined constant speed if the drive is not loaded.

2. A device for generating a multi-component dental compound comprising:

a mixer;

a plurality of parallel cartridges exchangeably mounted to open out into the mixer, each said cartridge containing a component of the multi-component dental compound and having a plunger; and an electric motor which commonly advances and returns the plungers, said electric motor having a load state when advancing said plungers and an unloaded state when returning said plungers; and a regulating unit which monitors the load state of the motor and maintains the motor at a predetermined constant speed when the motor is under load and at a higher speed in the absence of a load.

3. The device of claim 2, wherein said regulating unit detects a current demand of the motor to determine the load state of the motor.

4. The device of claim 2, wherein said plungers have an empty position relative to said device when said cartridges are empty and said device is provided with a sensor for detecting when said plungers are in the empty position.

5. The device of claim 2, wherein said mixer is a dynamic mixer.

6. The device of claim 5, comprising:

a mixer drive having a drive-side coupling part and a mixer-side coupling part, a load state and a no-load state, wherein said drive-side and mixer-side coupling parts are engaged by rotational movement of one of said drive-side and mixer-side coupling parts relative to the other of said drive-side and mixer-side coupling parts;

and said regulating unit is equipped to detect the load state of the mixer drive and maintain the mixer drive at a predetermined mixing speed when the mixer is under load and maintain the mixer drive at a coupling speed which is lower than said mixing speed when said mixing drive is in a no-load state.

7. The device of claim 6, wherein one of said drive-side or mixer-side coupling parts is resiliently displaceable in an axial direction counter to a spring force relative to the other of said drive-side or mixer-side coupling parts.

8. The device of claim 6, wherein said mixer drive is automatically stopped when said electric motor is returning said plungers.

9. The device of claim 2, wherein said mixer is a static mixer.

* * * * *